(12) United States Patent
Kassab et al.

(10) Patent No.: US 8,396,566 B2
(45) Date of Patent: Mar. 12, 2013

(54) DEVICES, SYSTEMS AND METHODS FOR PACING, RESYNCHRONIZATION AND DEFIBRILLATION THERAPY

(75) Inventors: Ghassan S. Kassab, Indianapolis, IN (US); Jose A. Navia, Sr., Buenos Aires, AR (US); Yunlong Huo, Indianapolis, IN (US)

(73) Assignee: CVDevices, LLC, Zionsville, IN (US)

( * ) Notice: Subject to any disclaimer, the term of this patent is extended or adjusted under 35 U.S.C. 154(b) by 544 days.

(21) Appl. No.: 12/307,110

(22) PCT Filed: Jun. 29, 2007

(86) PCT No.: PCT/US2007/015237
§ 371 (c)(1),
(2), (4) Date: Jun. 16, 2009

(87) PCT Pub. No.: WO2008/005386
PCT Pub. Date: Jan. 10, 2008

(65) Prior Publication Data
US 2010/0160988 A1    Jun. 24, 2010

Related U.S. Application Data

(60) Provisional application No. 60/817,424, filed on Jun. 30, 2006.

(51) Int. Cl.
*A61N 1/00* (2006.01)
*A61N 1/362* (2006.01)

(52) U.S. Cl. ............... 607/119; 607/2; 607/5; 607/115; 600/16; 600/17

(58) Field of Classification Search ................ 607/2, 5, 607/115, 119; 600/16–17
See application file for complete search history.

(56) References Cited

U.S. PATENT DOCUMENTS

| 5,170,784 | A | * | 12/1992 | Ramon et al. | ............. 607/9 |
| 5,697,285 | A | * | 12/1997 | Nappi et al. | ............. 91/519 |
| 7,610,092 | B2 | * | 10/2009 | Cowan et al. | ............. 607/33 |
| 2004/0267153 | A1 | * | 12/2004 | Bergethon | ............. 600/554 |

OTHER PUBLICATIONS

International Searching Authority, International Search Report, Aug. 25, 2008.
International Searching Authority, Written Opinion of the International Searching Authority, Aug. 25, 2008.

* cited by examiner

*Primary Examiner* — Nicole F Lavert
(74) *Attorney, Agent, or Firm* — Reichel IP LLP; Mark C. Reichel; Kevin R. Erdman

(57) ABSTRACT

Devices, systems, and methods for leadlessly stimulating the heart. Through a magnetic signal generator positioned outside or inside the thoracic cavity, a magnetic signal is transmitted through the chest to stimulate electrical activity within the myocardial muscles. The magnetic signal may function as a pacemaker, cardioverter or defibrillator. Advantages of magnetic stimulation include, without limitation, non invasiveness, a reduction or even elimination in pain, and access to tissues covered by poorly conductive structures.

33 Claims, 7 Drawing Sheets

DEVICES, SYSTEMS AND METHODS FOR PACING, RESYNCHRONIZATION AND DEFIBRILLATION THERAPY

RELATED APPLICATIONS

The present application is a U.S. National Stage Application of the International Patent Application Serial No. PCT/US07/15237, filed Jun. 29, 2007 and published as International Publication No. WO/2008/005386, which claims priority to U.S. Provisional Patent Application Ser. No. 60/817,424, filed Jun. 30, 2006. The contents of both of these applications are hereby incorporated by reference in their entirety into this disclosure.

BACKGROUND

Despite advances in techniques of resuscitation, cardiac arrest and related cardiac problems are associated with significant morbidity and mortality. Moreover, due to the incidence of sudden cardiac death ("SCD") and other life threatening cardiac ailments, cardiac dysfunction remains a major public health problem, especially for developed countries. For example, it is estimated that between 250,000 and 300,000 SCDs occur per year in the United States; an undoubtedly conservative estimate due to the fact that these figures are exclusively based on the assumption that about 50% of 600,000 cardiovascular deaths occur suddenly. (Myerburg and Spooner, 2001; Danieli G A, 2006). Moreover, according to recent trials, up to 50% of the deaths in patients with coronary artery disease and left ventricular systolic dysfunction are sudden or arrhythmic in nature. (Cannom D S, 2006). While the incidence of sudden or arrhythmic deaths is lower in patients with heart failure due to non-ischemic aetiologies, there is currently no way to detect which heart failure patients will die from an arrhythmia rather than progressive left ventricle systolic dysfunction. Although certain clinical markers such as greater age, degree of left ventricle systolic dysfunction, and severity of heart failure can predict general mortality, there is low specificity in detecting the mode of death.

A healthy cardiac rhythm not only consists of a heart that beats at the proper pace, but the muscular contractions of the four chambers of the heart must also be properly mediated such that they can contract in a coordinated fashion. The heart has specialized conduction pathways in both the atria and the ventricles that enable the rapid conduction of excitation (i.e. depolarization) throughout the myocardium. Normally, the sinoatrial node ("SA node") initiates each heart-beat cycle by depolarizing so as to generate an action potential. This action potential propagates relatively quickly through the atria, which react by contracting, and then relatively slowly through the atrio-ventricular node ("AV node"). From the AV node, activation propagates rapidly through the His-Purkinje system to the ventricles, which also react by contracting. This natural propagation synchronizes the contractions of the muscle fibers of each chamber and synchronizes the contraction of each atrium or ventricle with the contralateral atrium or ventricle.

The rate at which the SA node depolarizes determines the rate at which the atria and ventricles contract and thus controls the heart rate. The pace at which the SA node depolarizes is regulated by the autonomic nervous system which can alter the heart rate so that the heart, for instance, beats at a faster rate during exercise and beats at a slower rate during rest. The above-described cycle of events holds true for a healthy heart and is termed normal sinus rhythm.

The heart, however, may have a disorder or disease that results in abnormal activation that preempts sinus rhythm, and results in an irregular heartbeat, i.e. an arrhythmia. Individuals with cardiac ailments, and especially those at risk of SCD, may suffer from an irregular pace and/or uncoordinated mechanical activity wherein the myocardial depolarization and contraction of the chambers do not occur simultaneously. Without the synchronization afforded by the normally functioning specialized conduction pathways or the proper pacing by the SA node, the heart's pumping efficiency is greatly diminished and can thus compromise a patient's cardiac output. Several different factors may lead to the development of an arrhythmia, including atherosclerosis, thrombosis, defects in electrogenesis and nerve impulse propagation, influences of the sympathetic and parasympathetic systems, ischemia (inadequate oxygen supply to the cells due to lack of blood flow), and/or poor vascular control.

A variety of techniques are practiced to minimize the uncoordinated motion patients with cardiac ailments exhibit. Such current therapies can generally be divided into pharmacological, surgical, and electrical methods. While each of these therapies may be used individually, it is not uncommon for physicians to concurrently employ more than one. In addition, the physician's decision as to which type of therapy(ies) to employ depends, in large part, on the type of arrhythmia that the patient exhibits.

With respect to electrical therapy, catheter ablation and cardiac rhythm management devices have particularly evolved as the gold standard therapies for patients at high risk for ventricular and supraventricular tachyarrhythmia (i.e. abnormally rapid beating of the heart). Catheter ablation is an invasive procedure used to remove the faulty electrical pathways from the heart. The procedure consists of inserting several flexible catheters into the patient's blood vessels, typically into the femoral, internal jugular, or subclavian veins. The catheters are then advanced towards the heart and high-frequency electrical impulses are used to induce an arrhythmia, and then ablate (destroy) the abnormal tissue that is causing the arrhythmia. While catheter ablation of most arrhythmias has an extremely high success rate, the procedure is highly invasive and requires direct contact with the region of interest.

Cardiac rhythm management devices are implantable devices that provide electrical stimulation to selected chambers of the heart in order to treat cardiac rhythm disorders. There are numerous types of cardiac rhythm management devices, the most notable of which include pacemakers and implantable cardioverter defibrillator ("ICD") devices.

A pacemaker is a cardiac rhythm management device that paces the heart with timed pacing pulses. The simplest configuration of a pacemaker is a power source with a timing circuit and an electrical lead designed to carry electrical energy to the heart. The most common condition for which pacemakers are used is in the treatment of bradycardia, where the ventricular rate is slow. Pacing therapy may also be applied in order to treat cardiac rhythms that are too fast, termed anti-tachycardia pacing.

If functioning properly, the pacemaker makes up for the heart's inability to pace itself at an appropriate rhythm by enforcing a normal heart rate. It does this by using electrical energy to cause the myocardium to contract when necessary, as determined based off of a normal sinus rhythm. Currently, pacemakers are capable of "dual-chamber pacing", which initiates a contraction in the atrium, the ventricle, or both. When enough energy is sent down through the lead to cause depolarization in the myocardium, and therefore a contraction, "capturing" of the heart occurs and the depolarization effect can be observed on an electrocardiogram ("ECG"). As the term is used herein, "capture threshold" is the minimum amount of energy necessary to capture the heart.

An ECG of a normal sinus rhythm is characterized by a P wave, which corresponds with atrial depolarization and contraction of the atria, followed by the QRS complex, which corresponds with depolarization and contraction of the ventricles. Due to size differences between the atria and the ventricles, the P wave is considerably smaller than the QRS complex. A T wave follows the QRS complex and corresponds to ventricular repolarization. Atrial repolarization is difficult to detect with an ECG as the atrial repolarization signal has a small amplitude and is mainly hidden by the much larger QRST complex. In addition to the P wave and the QRST complex, a normal ECG is also characterized by a PR interval, defined as the time between atrial and ventricle contractions, of about 0.12 to 0.20 sections and regular R-R intervals, defined as the time between QRST complexes, of about 0.60 to 1 second.

The pacing rate of a pacemaker consists of the average number of pulses delivered from the power source over a specified period of time, usually one (1) minute. The length of time from one pacing impulse to the next is termed the pacing interval. It is the goal of using a pacemaker that the pacing interval eventually corresponds to the normal sinus rhythm discussed above. The pulse width, (measured in milliseconds), is the length of time that the current flows through the lead when the pacemaker delivers an energy pulse. Conventional pacemakers typically contain an internal timing clock to measure time in thousandths of a second, or milliseconds (ms), to ensure the pacing impulses are delivered correctly. The pacemaker's output is equal to the amount of energy delivered with each energy pulse. Energy can be considered as "voltage over time" or voltage at a certain pulse width. The optional capture thresholds can be calculated by varying the pulse width while maintaining a constant voltage.

Economically, cardiac pacemakers account for more than 50% of worldwide expenditure in the electrophysiology market, which includes cardiac pacemakers, ICDs, and radiofrequency ablation devices. (ANAES, 1999). In 1998, the percentage accounted for approximately $2.5 billion in sales, or approximately 540,000 implanted pacemakers. (ANAES, 1999). The number of cardiac pacemakers inserted continues to increase over time, especially in light of the ever-increasing elderly population.

Pacemaker implantation is a common surgical procedure that is performed under local anesthesia and requires only a short hospitalization time. A lead catheter is inserted into the chest, through the subclavian vein, which is located below the collarbone and above the heart. The pacemaker's leads are then threaded through the catheter and adhered to the appropriate chamber or chambers of the heart. The electrodes are typically positioned in contact with the inner surface of the right atrium or ventricle. The pacemaker's leads are then tested to guarantee that there is consistent capture with a sufficiently low energy level to ensure that the pacemaker can function properly over an extended period of time. Finally, a small pocket is created subcutaneously on the upper portion of the chest wall to hold the power source, which is thereafter closed with stitches. It is not uncommon for the power source—typically a conventional lithium battery—to be easily felt through the skin. Such lithium batteries typically exhibit a battery life of eight (8) to ten (10) years and are easily replaced by performing a relatively minor surgery where the subcutaneous pouch is reopened under local anesthesia.

A common problem with cardiac pacemaker implantation is dislocation of the leads, which typically occurs in 1.1% to 6% of all cases. (ANAES, 1999). This complication generally takes place within two (2) months of insertion and requires additional surgery to relocate the leads. In addition, the implantation of a pacemaker also carries the risks of developing haematoma, hemorrhage, perforations of the heart and the pleura, infection (more specifically, endocarditis), and symptomatic and asymptomatic venous thrombosis. Electrophysiological complications may also include pacemaker syndrome, an atrial fibrillation considered to be less common with single chamber atrial inhibited pacing mode cardiac pacemakers. In addition, the implantation procedure is invasive and requires direct contact with the region of interest.

In about 30% of chronic heart failure patients, the disease process compromises the myocardium's ability to contract, which thereby alters the conduction pathways through the heart and causes a delay in the beginning of right or left ventricular systole. (Abraham et al., 2002). On an ECG, such a desynchronization is manifested as a QRS complex interval lasting more than 120 ms. It has been proposed that intraventricular conduction delay may compromise the ability of the failing heart to eject blood and may consequently increase the severity of the mitral valve regurgitant flow. In patients with heart failure, the intraventricular conduction delay leads to clinical instability and an increased risk of death. These uncoordinated contractions cannot be remedied by a conventional pacemaker alone, as simple pacemakers merely address pacing issues. Currently, there are several devices that make use of atrial-synchronized biventricular pacing in order to coordinate right and left ventricular contraction.

A cardiac resynchronization therapy ("CRT") device, also known as a biventricular pacemaker, is a type of pacemaker that can pace both ventricles (right and left) of the heart. As noted above, by pacing both sides of the heart, the pacemaker can resynchronize a heart that does not beat in synchrony, which is common in patients at risk for SCD. After the Food and Drug Administration approved CRT in 2001, approximately 271,000 heart failure patients in the United States have received CRT for moderate to severe heart failure. (Aranda et al., 2005).

Conventional CRT devices closely resemble pacemakers, except that a typical CRT device has three (3) electrical leads which are coupled to cardiac tissue. The first lead is typically coupled to the right atrium, a second lead is typically coupled to the right ventricle, and a third lead is typically coupled to the left ventricle (often via the coronary sinus or great vein). Implantation and maintenance of a CRT device are linked to greater risks than conventional pacemaker devices. This is because a device delivering CRT requires that the third lead is inserted through the coronary sinus and advanced into the cardiac vein to pace the left ventricle. As a result, the risk of an unsuccessful implantation of the device or even dissection or perforation of the coronary sinus or cardiac vein is increased significantly. Erroneous efforts to implant the third lead or the device may also have severe complications, including complete heart block, hemopericardium, and even cardiac arrest. In addition, it is not uncommon for the left ventricular lead to become dislodged during long-term pacing, which necessitates repositioning or replacement of the lead.

An additional cardiac rhythm management device that is closely related to a pacemaker is the ICD device. Like CRT, ICDs resemble pacemakers and are often used in the treatment of patients at risk for SCD. An ICD is a small, battery powered electrical impulse generator which is typically implanted in patients who are at risk of SCD due to ventricular fibrillation. The principles of cardiac arrhythmia detection and treatment are incorporated into the implantable device, such that the ICD can monitor the heart's sinus rhythm and deliver the proper electrical treatment automatically.

An ICD has the ability to treat many types of heart rhythm disturbances (including uncoordinated cardiac activity) by means of pacing, cardioversion, or defibrillation. ICDs are capable of constantly monitoring the rate and rhythm of the heart and delivering therapies, by way of electrical shock, when the heart activity is not in accordance with the optimal sinus rhythm. In this manner, ICDs are able to offer joined therapy with programmable anti-arrhythmia pacing schemes, as well as low and high energy shocks in multiple ranges of tachycardia rates. Conventional ICD devices are considerably smaller than the first prototypes of the early 1980s and can easily be positioned under the skin in the left chest. The majority ICD generators must be replaced every four (4) to five (5) years.

In the United States in 2002, 415,780 ICD devices were implanted. (Wilkoff B L, 2007). The process of implantation of an ICD is similar to implantation of a pacemaker. Similar to CRT devices, these devices typically include electrode leads which pass through the coronary sinus and into the cardiac vein. Accordingly, the same risks that apply to the implantation and maintenance of pacemakers, and specifically CRT devices, are applicable to ICD devices.

Due to the growing number of patients requiring some form of cardiac rhythm therapies, there is a need for a technique that benefits from the advantages of ICDs and pacemakers without suffering the problems associated with such devices. Furthermore, such novel techniques should be easy to understand and implement, universally adoptable, and have competitive advantages over conventional heart treatment devices, such as ICDs and pacemakers.

Articles discussing cardiac disease and treatment include:

Abraham W T et al. Cardiac resynchronization in chronic heart failure. *N Engl J Med* 2002; 346(24):1845-1853.

Agence Nationale d'Accréditation et d'Évaluation en Santé. Evaluation clinique et économique des endoprothèses aortiques. Paris: ANAES; 1999.

Aranda et al. Management of heart failure after cardiac resynchronization therapy: integrating advanced heart failure treatment with optimal device function. *J Am Coll Cardiol* 2005; 46(12): 2193-98.

Cannom D S. "After DEFINITE, SCD-HeFT, COMPANION: Do We Need to Implant an ICD in All Patients With Heart Failure?" Cardiac Arrhythmias Proceedings of the 9th International Workshop on Cardiac Arrhythmias. A. Raviele. Venice 425-434 (2005).

Danieli G A. "Sudden Arrhythmic Death: Which Genetic Determinants?" Cardiac Arrhythmias Proceedings of the 9th International Workshop on Cardiac Arrhythmias. A. Raviele. Venice 385-392 (2005).

Myerburg R J, Spooner P M. Opportunities for sudden death prevention: directions for new clinical and basic research. *Cardiovasc Res* 2001; 50: 177-85.

Wilkoff B L. Pacemaker and ICD malfunction—an incomplete picture. JAMA 2007; 295(16): 1944-1946.

SUMMARY

Devices, systems, and methods for the magnetic resynchronization of a heart are provided. Embodiments of the device include an external source of magnetic energy to resynchronize the heart to initiate or correct proper sinus rhythm. By determining the proper level of energy required to resynchronize the sinus rhythm, devices transmit a magnetic energy wave to the heart to retrigger the electrical pattern necessary to re-initiate the pattern for contraction.

An additional embodiment comprises a device for stimulating the heart. The device comprises a magnetic signal generator positioned outside of a chest cavity. When the magnetic signal generator produces a magnetic signal external to the chest cavity, the heart receives the magnetic signal and resets its electrical activity accordingly.

To prevent attenuation and loss of energy when the device is situated externally of the chest cavity, the device may be implanted adjacent to the heart using a minimally invasive procedure, and/or the standard cardiac surgical procedure. Standard thorascopic techniques can be employed to implant and anchor the device onto the pericardium immediately near the heart.

An additional embodiment comprises a method for determining treatment for a heart. The method includes determining the heart rate and arrhythmia information; analysis of the information to determine best therapeutic strategy; and applying magnetic stimulus that corresponds with the determined best therapeutic strategy.

DETAILED DESCRIPTION

Figure 1:
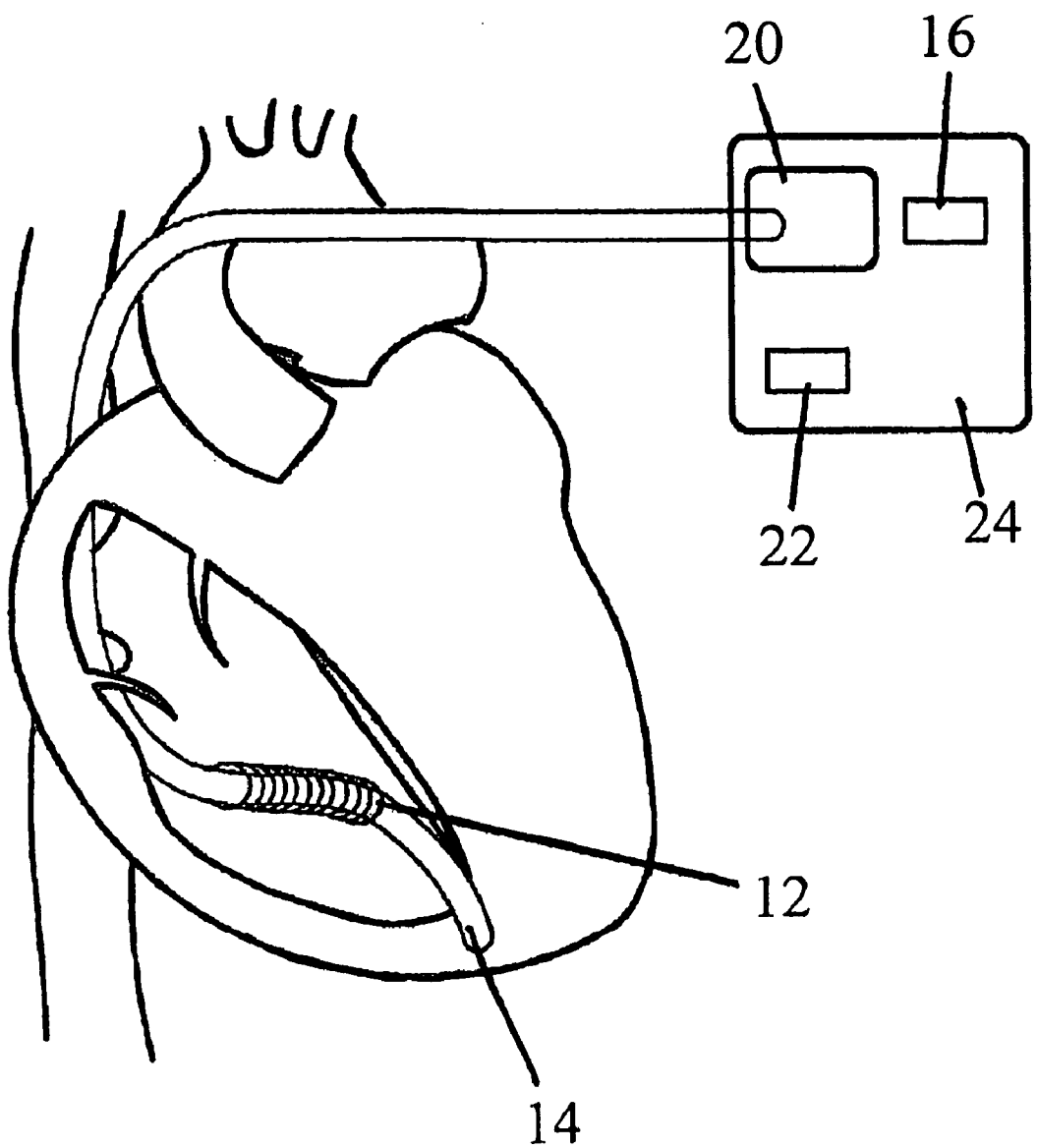
FIG. 1 shows a partial cross-section view of an implantable cardioverter defibrillator of the PRIOR ART.

Reference will now be made to the embodiments illustrated in the drawings and specific language will be used to describe the same. It will nevertheless be understood that no limitation of scope is intended by the description of these embodiments.

FIG. 1 shows a partial cross-section view of an implantable cardioverter defibrillator 10 ("ICD 10") of the prior art. The ICD 10 of the prior art comprises a pulse generator 16, at least one shock coil 12, and at least one spacing electrode 14. The pulse generator 16 is capable of generating the electrical pulse that is used to deliver therapy to the heart 50 through the shock coil 12. The pulse generator 16 comprises a circuitry 20 and a battery 22 encased within a hermetically sealed, biologically inert outer casing 24 and is typically implanted either beneath the skin in the subcutaneous space or beneath the pectoral muscles, adjacent to the heart 50.

One or more shock coils 12, collectively identified with reference to numeral 12 in FIG. 1, are electrically coupled to the pulse generator 16 in a conventional manner and extend transvenously between the implant site of the pulse generator 16 to the heart 50. Disposed near the distal end of the shock coils 12 are one or more exposed spacing electrodes 14 for receiving electrical cardiac signals and/or delivering electrical pacing stimuli to the heart 50. The shock coils 12 of the ICD 10 are implanted with their distal end(s) situated in the atrium and/or ventricle of the heart 50. In addition, at least one of the shock coils 12 is typically advanced into the cardiac vein such that the ICD 10 to pace the left ventricle. In operation, the ICD 10 of the prior art delivers electrical stimuli directly to the heart 50 through the shock coils 12 and, ultimately, the pacing electrodes 14. While the application of direct-electrode stimulation does not present many difficulties with respect to localizing the proper area of the heart to be stimulated, the direct-electrode treatment is often considerably painful for the patient.

To implant the ICD 10 into a patient, the shock coils 12, and therefore the pacing electrodes 14, must be inserted into various veins associated with the heart, including the cardiac vein. Insertion of a lead into the cardiac vein is a particularly invasive procedure, as the shock coil 12 must first be inserted through the coronary sinus and thereafter advanced into the cardiac vein. As previously noted, the pulse generator 16 is also implanted into the patient, either subcutaneously in between the skin and the ribs, or in the proximity of the heart 50 itself. In the event the pulse generator 16 is implanted adjacent to the heart 50, the battery 22 is typically implanted subcutaneously so that the battery 22 can be easily accessed and replaced upon failure. When the battery 22 is implanted subcutaneously and independent of the pulse generator 16, an additional lead is run from the battery 22 to the pulse generator 16.

Figure 2A:
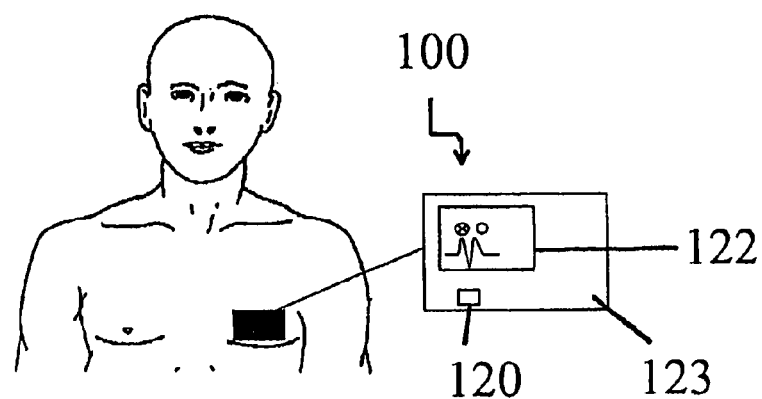
FIG. 2A shows a front view of a magnetic cardioverter defibrillator device.
Figure 2A:
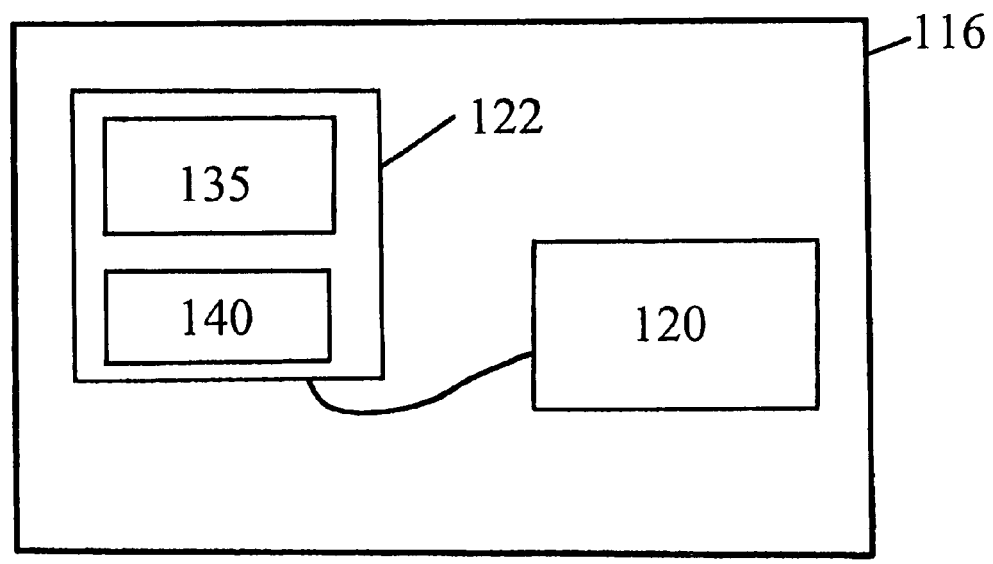
Figure 2B:
FIG. 2B shows a schematic diagram of the magnetic cardioverter defibrillator device of FIG. 2A.

Now referring to FIGS. 2A and 2B, a novel magnetic cardioverter defibrillator 100 (the "MCD device 100") is shown. The MCD device 100 is capable of implementing leadless magnetic therapy to a heart, even when positioned externally of the patient's chest cavity. Accordingly, the MCD device 100 offers a less invasive alternative to conventional devices and methods. Moreover, because the therapy is delivered by magnetic stimulation, the use of the MCD device 100 may reduce the amount of pain felt by a patient when the therapy is applied. This is because with direct-electrode stimulation, the current required to stimulate a region of the myocardium must pass through the highly resistive myocardial muscle cells, which contain numerous pain fiber endings. However, with the magnetic stimulation delivered by the MCD device 100, the electric field is circumferential and tangential to the myocardial muscle, thereby necessitating less current density, therefore resulting in less sensation.

The MCD device 100 comprises a pulse generator 116 having a power supply 120 and circuitry 122, both of which are encased within a casing and shield 123. The casing and shield 123 are hermetically sealed and biologically inert, such that the casing and shield 123 protect the components contained therein, and do not interfere with the magnetic stimulation generated by the pulse generator 116.

Figure 3:
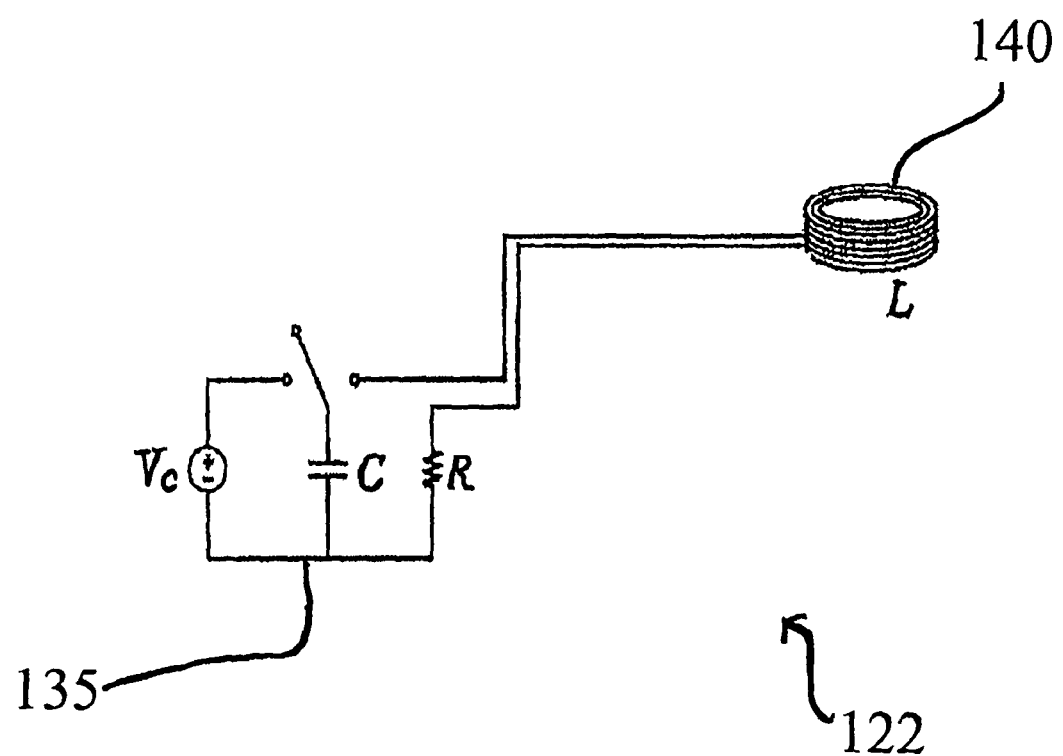
FIG. 3 shows a schematic diagram of one embodiment of a circuitry of the magnetic cardioverter defibrillator device of FIG. 2A.

The power supply 120 may comprise any power supply known in the art, so long as power supply 120 is capable of providing sufficient power to the pulse generator 116 over a period of time. In one embodiment, the power supply 120 comprises a lithium battery. The circuitry 122 is electronically coupled with the power supply 120 and comprises a magnetic stimulation system having a magnetic stimulator 135 and at least one coil 140. The magnetic stimulator 135 and the at least one coil 140 form a circuit 122, which in one embodiment is a series resonant or RLC circuit (as shown in FIG. 3). While the RLC circuit of FIG. 3 is offered by way of an example, it will be understood that any type of circuit may be used in conjunction with the magnetic stimulation system, including more complicated circuits. The magnetic stimulation system, by way of the magnetic stimulator 135 and the coils 140, produces magnetic stimulation in cardiac muscle through the transmission of electromagnetic fields.

The magnetic stimulator 135 is capable of generating pulse fields by delivering current into the coil 140. The configuration of the coil 140 and the magnetic stimulator 135 may affect the different values of capacitance available. For example, in one embodiment the magnetic stimulator 135 further comprises a high-powered thyristor and can thereby control the capacitor discharge. When the number of coils 140 (inductors) are increased (see FIG. 4C), the magnetic stimulator 135 may further comprise parallel capacitors to generate high magnetic localization.

Now referring to FIGS. 4A-4D, different configurations of the coils 140 are shown. The coils 140 of the circuitry 122 may comprise several possible configurations. Numerous factors may influence the optimal coil 140 configuration, such as the placement of the MCD device 100 relative to the heart, the patient's body composition, and/or specific details with respect to the arrhythmia being treated. Different coil configurations can create different stimulation on the epicardium. In addition, the numerous muscles and bones located in the chest can reflect and refract the electromagnetic fields produced by the magnetic stimulation system. Therefore, the adaptation of the magnetic coils 140 to aid in the localization of the electromagnetic field is beneficial. Alternatively, implantation of the MCD device 100 adjacent to the heart circumvents issues of refraction and reflection while nonetheless having the less invasive advantage of remaining outside of the heart or vessels.

Figure 4A:
FIG. 4A shows a bottom view of one embodiment a coil configuration for use with the magnetic cardioverter defibrillator device of FIG. 2A.
Figure 4B:
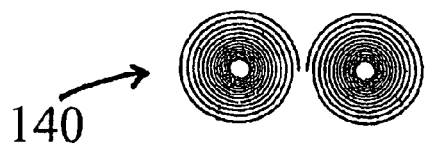
FIG. 4B shows a bottom view of an additional configuration of the coil of FIG. 4A.
Figure 4C:
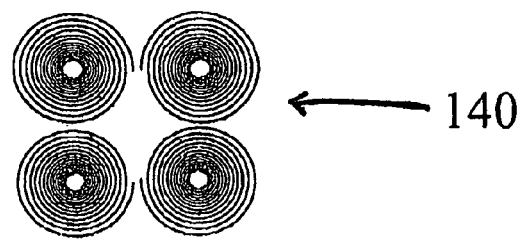
FIG. 4C shows a bottom view of an additional configuration of the coil of FIG. 4A.
Figure 4D:
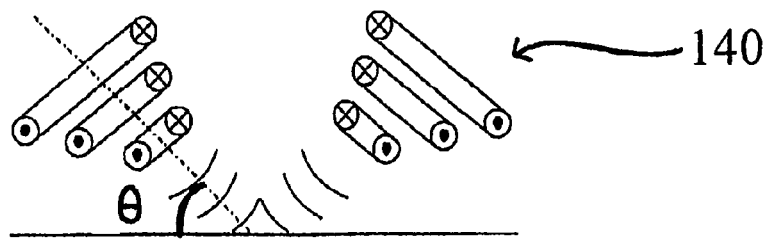
FIG. 4D shows a side view of the coil configuration of FIG. 4B.

In one embodiment of the MCD device 100, the coils 140 are individually configured into circular flat-spiral coils, as shown in FIG. 4A. While a single coil 140 may be used in this configuration in the magnetic stimulation system to produce a magnetic signal, a plurality of coils 140 arranged in various configurations relative to each other may also be employed. FIGS. 4B, 4C, and 4D illustrate two (2) possible configurations of the at least one coil 140 that is used in the MCD device 100. While only two configurations are discussed herein, it will be recognized that any number of coil designs may be used with the magnetic stimulation system of the MCD device 100. In FIGS. 4B and 4D, two of the coils 140 are arranged in a two-leaf, butterfly configuration. In FIG. 4C, four of the coils 140 are arranged in a four-leaf, cloverleaf configuration. As previously noted, these different coil configurations create different stimulus on the epicardium. For example, the flat-spiral coil (shown in FIG. 4A) induces currents similar to those induced by the larger coil configurations, but more focally. The butterfly-shaped coil (shown in FIGS. 4B and 4D) induces the largest currents in its center, where the circumferences of the two component coils 140 adjoin. In addition, the butterfly-shaped coil configurations (FIGS. 4B and 4D) and the cloverleaf-shaped coil configurations (FIG. 4C) are more efficient than a single circular coil, such as the one shown in FIG. 4A. In short, the different geometries of the coils 140 affect the values of the magnetic induction and electric field induced by the MCD device 100.

The MCD device 100 may either be implanted within a patient's thoracic cavity, or positioned externally. In both locations, the MCD device 100 is capable of leadlessly transmitting an electric pulse to the myocardial fiber by inducing time-varying magnetic fields. Referring back to FIG. 2A, the MCD device 100 is positioned external to the patient's body. The external MCD device 100 may be employed in clinical settings or may be affixed to the exterior of a patient's chest for outpatient therapy. In this manner, the patient can benefit from the therapy delivered by the MCD device 100 without undergoing invasive surgery and risking the numerous complications associated therewith. Moreover, because the MCD device 100 is external to the patient's body, the power supply 120 can be easily replaced and recharged.

In an alternative embodiment, the MCD device 100 may be implanted within the patient's thoracic cavity to provide more comfort and security to the patient. Because the MCD device 100 does not require direct contact with the heart, the MCD device 100 may be implanted subcutaneously in between the patient's skin and ribs, on the surface of the heart or pericardium, or any other location within the body where the MCD device 100 can effectively transmit the generated electric pulses to the heart. In any of the embodiments where the MCD device 100 is internal to the patient's body, the power supply 120 may be attached to the MCD device 100 through a wire and subcutaneously implanted independently of the MCD device 100 such that the power supply 120 can be easily accessed and replaced or recharged when necessary.

In operation, the MCD device 100 is capable of treating arrhythmias through the use of localized magnetic stimulation. The magnetic stimulation system of the circuitry 122 may either be programmed to initiate stimulus at a specific time or, in the embodiment where the MCD device 100 is located outside of the patient's body, the magnetic stimulation system of the circuitry 122 may be manually activated. When the MCD device 100 is activated, the electric current in the myocardial fibers of the patient's heart are induced by the magnetic coils 140 within the circuitry 122. If the circuitry 122 comprises an RLC circuit (as shown in FIG. 3), the optimal amount of current i(t) to run through the coil(s) 140 can be determined by the ordinary differential equation associated with an RLC circuit, as given in Equation 1. The duration of the first phase of di(t)/dt is denoted as the pulse width of a magnetic stimulus.

$$i(r, t) = V_0 C \omega_2 e^{-\omega_1 t}\left(\left(\frac{\omega_1}{\omega_2}\right)^2 + 1\right)\sinh(\omega_2 t) \quad [1]$$

where $$\omega_1 = \frac{R}{2L} \text{ and } \omega_2 = \sqrt{\left(\frac{R}{2L}\right)^2 - \frac{1}{LC}}$$

and C and R are the default capacitance and inductance, respectively, and $V_0$ is the initial voltage. The total resistance of the RLC circuit includes the default and coil resistances.

As the current flows through the coil(s) 140, the induced electric field E(r, t) and magnetic induction B(r,t) can be calculated from the coil current and the geometry of the coil(s) 140 by Equation 2.

$$E(r, t) = \left(\frac{di(r, t)}{dt}\right)\left(-\frac{\mu_0 N}{4\pi}\int \frac{dl'}{|r - r'|}\right) \quad [2]$$

$$B(r, t) = \nabla \times \left(\frac{\mu_0 N i(r, t)}{4\pi}\int \frac{dl'}{|r - r'|}\right) \quad [3]$$

where $\mu_0$ is a constant (4 $\pi \times 10^{-7}$ V·s/AM);
N is the number of turns in the coil 140;
i(r,t) is the coil current;
r is the position where the electric field is calculated;
r' is the position of the differential element of the coil dl'.

The induced electric field can be expressed as the product of a function of time and space without considering the electrostatic potential. Once the coil geometry has been prescribed, the spatial distribution of the electric field can be determined independently of the current using the integral of Equation 2. In addition, Equations 1 and 2 are used to determine any term in the magnetic stimulation system when other values are defined.

As previously noted, the MCD device 100 can be programmed to implement various designed programs to deliver timed magnetic stimulation by controlling the circuitry 122 in the MCD device 100. Antitachycardia pacing ("ATP") is a conventional electrophysiological technique that is commonly used for terminating monomorphic tachycardias. The ATP techniques can be delivered by the MCD device 100 and involve lowest-energy short pacing pulse (synchronized stimuli) delivered with a cycle length of approximately 80-90% of that of the tachycardia. By delivering pulses at a pace slower than the heart is beating, the ATP attempts to terminate the ventricular and supraventricular tachycardia. In practice, dual pacing has been shown to result in significant haemodynamic improvement.

The two basic modes of antitachycardia pacing include 1) overdrive burst pacing, and 2) autodecremental ("ramp") pacing. For these two major modes of ATP, different features can be added, such as the coupling interval scan, start interval scan, programmed extrastimulus, and additional extra pulses. Ramp pacing has been reported to be more efficacious than burst pacing in terminating sustained monomorphic ventricular tachycardia and has exhibited a low incidence of accelerating ventricular tachycardia. In addition, antibradycardia pacing can also be implemented by the MCD device 100 via ATP.

The ATP current used to depolarize the heart is generally <5 mA for the ventricles, which can be up to 20 mA. The pulse width, or the duration which the voltage is applied to the heart thereby causing current flow, is determined by the length of time it takes for the capacitor to discharge. In the MCD device 100, the pacing pulse corresponding to the induced electrical field (E(r,t) in Equation 2) is controlled by the pulse of a magnetic stimulus (di(r,t)/dt). The pulse width is generally around 1 ms because the longer the pulse width, the greater discharge of energy per pulse and the shorter the battery life. The pulse amplitude (potential) required to capture the heart is about 200 mV on the epicardium. The potential gradient (the electric field intensity) is generally 100 mV/cm.

Given the necessary pacing parameters (e.g., pulse current, pulse width, pulse amplitude), the required current in the magnetic coil(s) 140 can be inversely computed using Equations 1, 2, and 3. From Equation 2, the electric current (i(r,t)) in the magnetic coil(s) 140 can be calculated to equal approximately 1-10 A if a circular coil configuration is considered with N=30 turns, having an inner and outer radius of about 3 cm with butterfly configuration. From Equation 1, the battery potential $V_0$ can be calculated to equal approximately 20-50 V, assuming that C=200 μF and R=3Ω. C and R are the default capacitor and inductance, respectively, which are used to control the pulse width.

In the event that the tachycardia does not respond to ATP, the MCD device 100 is also capable of implementing low energy shocks, or cardioversion, in an initial attempt to terminate ventricular and supraventricular tachycardia while inducing minimal pain to the patient (as some patients remain conscious despite rapid tachycardia). Synchronized cardioversion is shock delivery that is timed (synchronized) with the QRS complex. Low energy cardioversion consists of synchronized shocks with energies of 1 J or less and may exhibit very short charge times. The corresponding electric field intensity is about 1 V/cm, which is ten times larger than pacing. Like pacing, every synchronized shock is controlled by the magnetic stimulus (di(t)/dt). The parameters associated with di(t)/dt are also C, R, and $V_0$ of Equation 1. The electric current (i(r,t)) and potential $V_0$ in the magnetic coils are respectively about 10-100 A and 200 V if the same RLC circuit is selected as was in pacing. However, low energy cardioversion delivered by the conventional direct-electrode devices may accelerate the tachycardia and is uncomfortable for the patient. As previously indicated, when the MCD device 100 is employed, the pain to the patient may be significantly reduced due to the use of magnetic stimulation as opposed to the electric stimulation of the prior art devices.

When low energy cardioversion fails, defibrillation may be delivered by the MCD device 100 to correct the serious tachycardia such as rapid ventricular tachycardia. In defibrillation delivered by conventional direct-electrode devices, four to eight non-synchronized shocks are applied and maximum shock energies range between 25 and 42 J with biphasic waveforms. When the MCD device 100 is used to deliver defibrillation, the corresponding electric field intensity is about 6 V/cm and 4 V/cm for a typical monophasic waveform and biphasic waveform, respectively. Like the low energy therapies, the non-synchronized shocks are also controlled by the magnetic stimulus (di(t)/dt). The parameters associated with di(t)/dt are also C, R, and $V_0$ of Equation 1. The electric current (i(r,t)) and potential $V_0$ in the magnetic coils are about 500 A and 1000 V, respectively, if the same RLC circuit is selected as was in pacing. More exact values for current and voltage may be determined based on the geometry of the coils 140 and the characteristics of the patient (for example, age, weight, thickness of chest, etc.), and will be apparent to one of ordinary skill in the art in view of the present disclosure.

Figure 5:
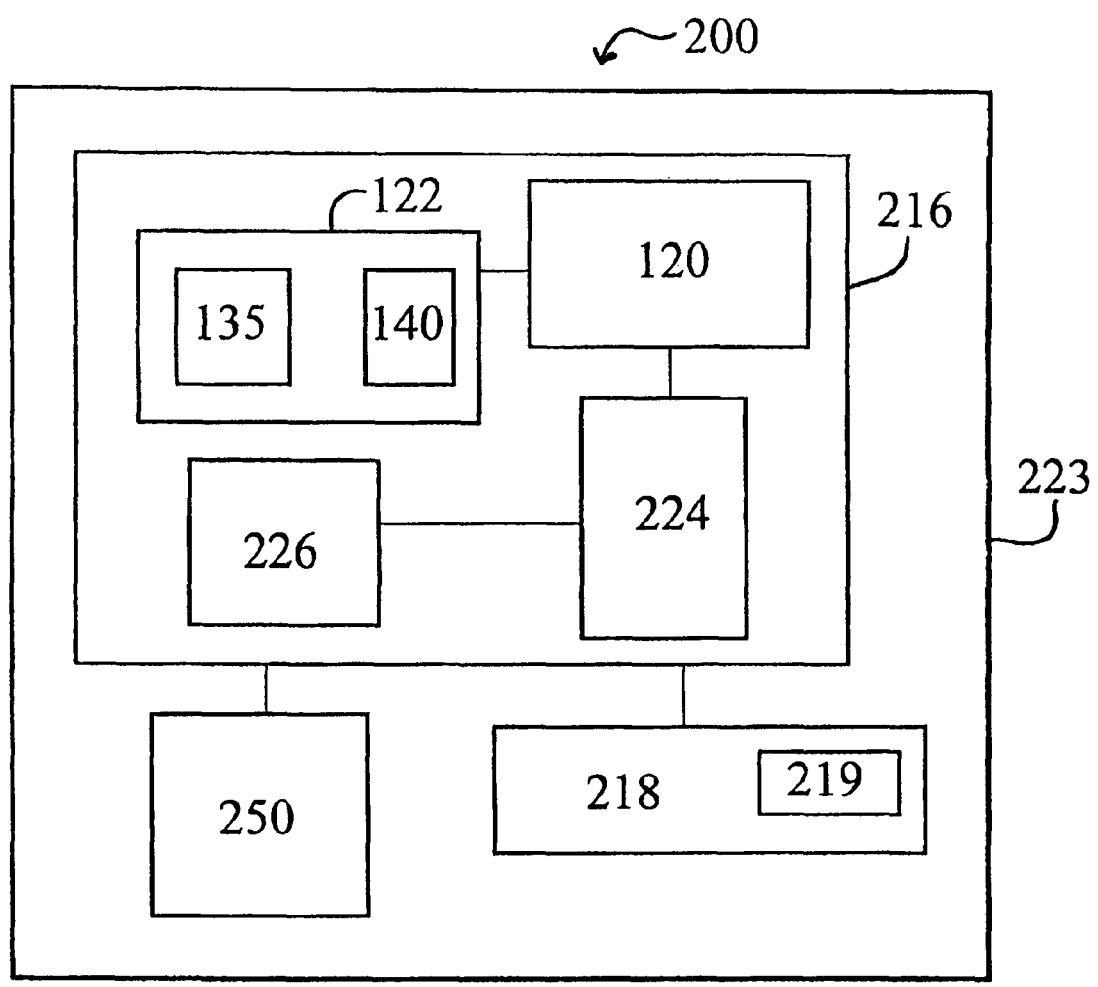
FIG. 5 shows a schematic diagram of one embodiment of a magnetic cardioverter defibrillator device and system.

Now referring to FIG. 5, a schematic diagram is shown of a magnetic cardioversion defibrillator system 200 (the "MCD system 206"). The MCD system 200 comprises an echo and adjustment system 250 and a magnetic cardioversion defibrillator device 223 (the "MCD device 223"), which comprises a pulse generator 216 and a plurality of leads 218. The echo and adjustment system 250 is capable of recording the position and motion of the walls and/or internal structures of the heart by the echo obtained from beams of ultrasonic waves directed through the chest wall.

In one embodiment, the echo and adjustment device 250 further comprises an x-ray device (not shown). In this embodiment, the x-ray device detects the position and motion of the heart walls and/or the internal structures using electromagnetic radiation. Using the information determined by the x-ray device, the echo and adjustment system 250 is capable of accurately calculating the optimal stimulation position in the beating heart by determining the simple geometrical computation |r-r'| of Equations 2 and 3. In this manner, the echo and adjustment system 250 allows for a user to determine if optimal levels of localization have been reached upon magnetic stimulation the tissue, or if the MCD device 223 needs to be redirected or modified in some way.

The pulse generator 216 comprises a power supply 120, circuitry 122, a microprocessor 224 for signal filtering and analysis, and at least one memory device 226 for data storage. Similar to the MCD device 100 previously discussed, all of the various components of the MCD device 223 may be encased within a casing and shield 123 (not shown). The casing and shield 123 are hermetically sealed and biologically inert, such that the casing and shield 123 protect the components contained therein, and do not interfere with the magnetic stimulation generated by the pulse generator 216. However, it is understood that the microprocessor 224, the plurality of leads 218, and/or the at least one memory device 226 may each comprise an independent device, separate and apart from the MCD device 223, so long as such devices are capable of being in communication with the MCD device 223.

The circuitry 122 and the power supply 120 may be identical to the components of the MCD device 100 shown in FIGS. 1-4D, and as such, will not be discussed in detail with respect to the MCD device 223. The microprocessor 224 is electronically coupled with the power supply 120 and the memory storage device 226. The microprocessor 224 may be any microprocessor known in the art that is capable of receiving and processing electrogram data. The memory device 226 is coupled with the microprocessor 224 and may be any memory device 226 known in the art that comprises an accessible database or other storage medium. In addition, the memory device 226 is capable of storing information collected from the heart and/or information stored therein by a user, such as therapeutic algorithms and/or an individual's cardiac sinus rhythm characteristics. In one embodiment, the memory device 226 comprises a plurality of memory chips to store the collected electrograms. In addition, in this embodiment, the memory device 226 is telemetrically accessible by a user, as is known in the art, such that a user may remotely access the collected electrograms stored within the memory device 226 even when the MCD device 223 is implanted in the patient's thoracic cavity.

The microprocessor 224 further comprises a plurality of leads 218, each lead 218 comprising at least one electrode 219 that functions as a sensor for detecting the electrical activity of the heart. The leads 218 and electrodes 219 may be any leads and electrodes known in the art that are capable of transmitting a continuous uptake of sinus rhythm information from a heart being monitored. The electrodes 219 may comprise any single electrode or combination of electrodes conventionally used to generate an electrogram and/or pacing signals, or the electrodes 219 may comprise other types of skin electrodes. The electrodes 219 produce electrical signals based on the electric fields generated by the heart and the leads 218 transmit these signals back to the microprocessor 224 for analysis. In this manner, the microprocessor 224 is able to track and analyze the condition of the heart in an automated fashion solely from the information received from the leads 218. While the leads 218 and electrodes 219 of the MCD device 223 are in close proximity to the cardiac muscle, it is not necessary for the leads 218 or electrodes 219 to be inserted into the cardiac muscle or veins, and the leads 218 and electrodes 219 are not required to deliver pacing and shocking pulses to the myocardium.

In one embodiment of the MCD system 200, the information collected through the leads 218 and electrodes 219 is used to create a real-time display of the intracardiac electrograms, which are thereafter used to assess the effect of body position and maneuvers on the electrical signals of the heart. In the event an abnormal sinus rhythm is observed, the echo and adjustment system 250 scans the heart using the x-ray device and automatically responds and redirects the MCD device 223 to the optimal stimulating position.

Similar to the MCD device 100, the MCD device 223 may be implanted within a patient's thoracic cavity, or the MCD device 223 may be positioned externally. The placement of the leads 218 and corresponding electrodes 219 relative to the heart depend on whether the MCD device 223 is positioned internally or externally relative to the patient's body. In one embodiment, the MCD device 223 is implanted in the patient's chest and the leads 218 extend to the pericardium between the pulse generator 216 and the patient's heart.

In an alternative embodiment where the MCD device 223 is implanted in the patient's chest, the leads 218 and electrodes 219 are implanted subcutaneously, but are not in direct contact with the heart. In this manner, the leads are not placed within the coronary sinus, cardiac vein, or any other vein of the heart, which results in a much less invasive procedure and significantly decreases the risk of complications. In yet another embodiment, both the MCD device 223 and the leads 218 are positioned outside of the patient's chest cavity. In this embodiment, the electrodes 219 of the leads 218 comprise, for example, skin electrodes, and the leads 218 are removably applied to the external portion of the patient's chest in a manner commonly known in the art.

In operation, the MCD device 223 is used to leadlessly transmit magnetic stimulation to initiate a reaction in the myocardium. The MCD device 223 generates the magnetic stimulation identically to the MCD device 100 of FIGS. 2A and 2B. In addition, optimal placement and configuration of the coil(s) 140 of the MCD device 223 is important to achieving an optimally localized magnetic field. For example, the MCD device 223 may be used to deliver continuous antitachycardia or antibradycardia pacing and defibrillation shock. Accordingly, when the optimal positioning is located, the signal is "localized" and the MCD device 223 need only use a minimum amount of energy to produce the desired effect. Generally, the optimal positioning of the MCD device 223 is perpendicular to the stimulation site. However, because of the likelihood of physical variation between individual patients, the MCD device 223 may be positioned such that the magnetic waves are focused, or localized, on the desired site of the heart. In this manner, the MCD system 200 may be optimally "tuned" to minimize the overall energy expenditure of the system.

Unlike the MCD device 100, the MCD device 223 of the MCD system 200 is employed in connection with the echo and adjustment system 250. Through the assistance of the echo and adjustment system 250, the MCD system 200 can automatically adjust the magnetic stimulation to modify the location and direction of the strongest portion of the electric pulse directed at the myocardium. As is the case with the MCD device 100, the direction of the electric pulse can be changed by adjusting the RLC circuit. For example, when defibrillation is applied to cardiac tissue, the efficacy rate of defibrillation in ventricular and supraventricular fibrillation by the use of biphasic waveforms is known to be higher than 98%, maximum shock energies range between 25 J and 42 J, and the mean energy needed for successful defibrillation is approximately 10 J. The preferred biphasic waveform is controlled by the duration of the first phase of di(t)/dt. When the energy requirement for electric shock is known from the detection procedure in the MCD system 200, the initial charged voltage ($V_0$) in the power supply 120 can be calculated with Equations 1 and 2, the capacitor and inductance (C and R) can be determined from the geometry, position, and direction of the coil(s) 140 in the RLC circuit, and further, if the number of turns of the coils 140 are optimally designed. Therefore, through the use of the echo and adjustment system 250 and Equations 1 and 2, the optimal localization of the MCD device 223 may be determined.

Figure 6A:
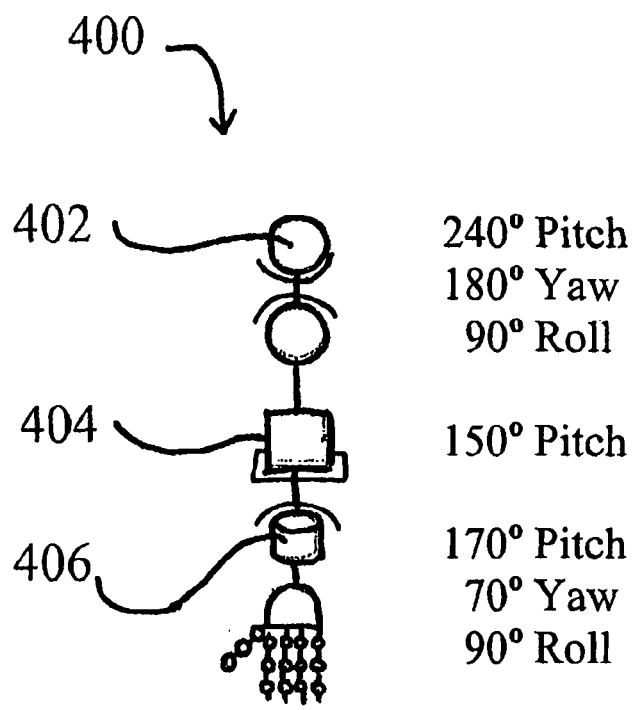
FIG. 6A shows a schematic diagram of a robotic arm for use with the magnetic cardioverter defibrillator device and system of FIG. 5.
Figure 6B:
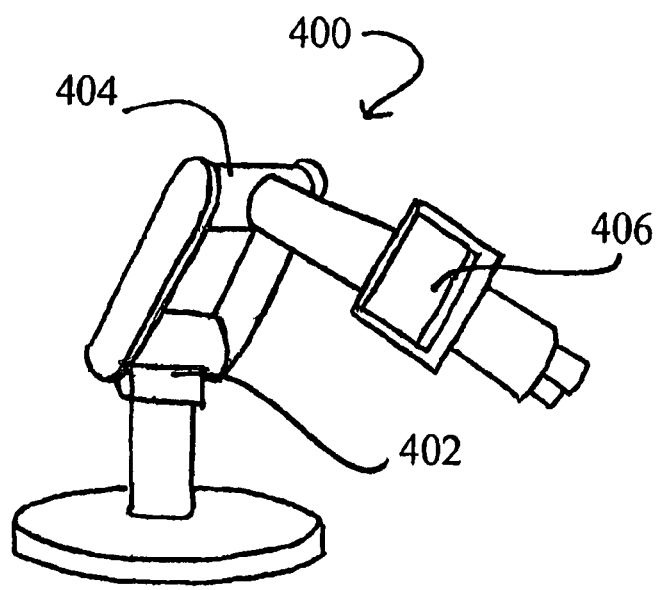
FIG. 6B shows a perspective view of the robotic arm of FIG. 6A.

In one embodiment of the MCD device 223, the circuitry 122—and more specifically the coils 140—may be fixed on a robotic arm 400 that is controlled by an electric motor (not shown). One embodiment of the robotic arm 400 is shown in FIGS. 6A and 6B. FIG. 6A depicts a two dimensional, schematic representation of the robotic arm 400, and FIG. 6B shows a three dimensional perspective view of the robotic arm 400. In this embodiment, the robotic arm 400 has seven (7) degrees of freedom. A shoulder 402 gives pitch, yaw and roll, an elbow 404 allows for pitch, and a wrist 406 allows for pitch, yaw and roll. As used herein, pitching is defined as tilting up and down, yawing is defined as turning left and right, and rolling is tilting from side to side. In one embodiment where the MCD device 223 is positioned externally, the MCD device 223 is coupled with the wrist 406 of the robotic arm 400 such that the robotic arm 400 is capable of automatically adjusting the position of the MCD device 223 relative to a heart to be treated. The robotic arm 400 may also be used in conjunction with the echo and adjustment system 250 and the detection algorithms to achieve optimal localization of the magnetic stimulus on the heart.

Figure 7:
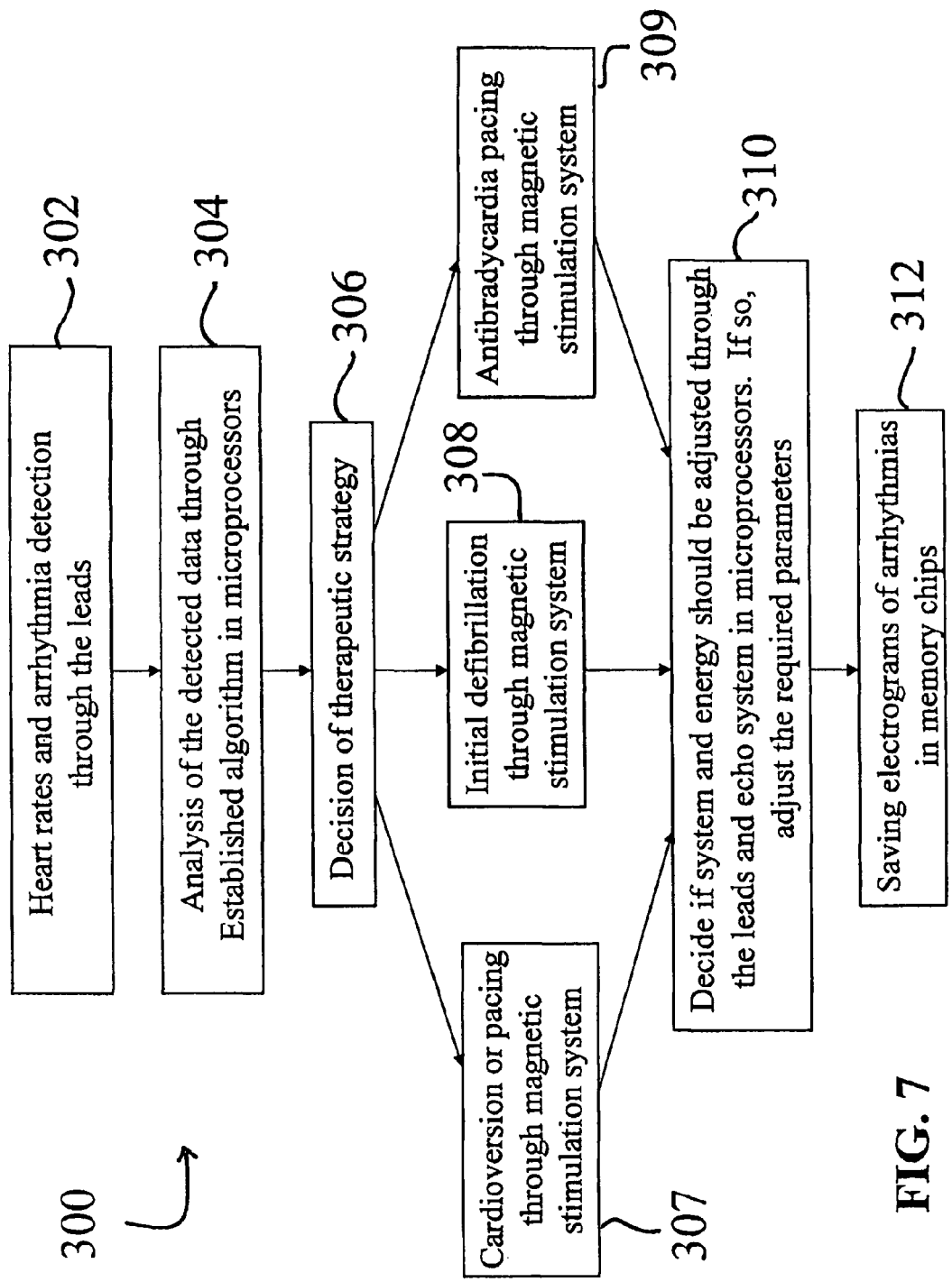
FIG. 7 shows a flow chart showing logic and functions steps of a method for treating arrhythmias over time.

FIG. 7 shows a flow chart of one embodiment of a magnetic cardiac stimulation method 300 (the "method 300") for providing noninvasive magnetic stimulation to cardiac muscle. For ease of understanding, the steps of the related methods described herein will be discussed relative to components of the MCD system 200 shown in FIG. 5, but it will be appreciated by one skilled in the art that any such system can be used to perform these methods so long as it is capable of leadlessly transmitting magnetic stimulation to cardiac tissue.

Generally, a user (for example, a physician) can utilize the MCD system 200 shown in FIG. 5 to perform at least three major functions: 1) arrhythmia detection; 2) arrhythmia treatment (for example, pacing, resynchronization, and defibrillation) with echo adjustment; and 3) episode data storage. As shown in FIG. 7, the leads 218 and corresponding electrodes 219 continuously collect electrogram information from the patients being monitored and/or treated by the MCD device 223 at step 302. As the leads 218 and electrodes 219 collect the information, the data is transferred to the microprocessor 224. In one embodiment, the leads 218 and electrodes 219 collect two main rhythm characteristics—heart rate and arrhythmia duration.

At step 304, the microprocessor 224 analyzes the collected data using established algorithms loaded on the microprocessor 224. In one embodiment, proper heart rate characteristics are programmed on the microprocessor 224 such that the microprocessor 224 simply compares the collected data against the program standard. Especially in the embodiment where the two rhythm characteristics are collected, the standard heart rate criterion can aid the microprocessor 224 in distinguishing an arrhythmia from a normal sinus rhythm. In addition, in view of the arrhythmia duration data, the microprocessor 224 is able to avoid falsely taking into account and initiating magnetic stimulation for a non-sustained arrhythmic episode.

When the microprocessor 224 identifies the specifics of the arrhythmia, the method 300 proceeds to step 306 and a decision is made with respect to the appropriate therapeutic response for the patient being monitored. In one embodiment of the method 300, this decision making step 306 is solely automated and performed by the microprocessor 224. For example, if the microprocessor 224 determines after analyzing the data received from the leads 218 that the patient is suffering from tachycardia and fibrillation, the microprocessor 224 automatically determines that the proper response to tachycardia and fibrillation is to either employ ATP, cardioversion (synchronized shocks), or defibrillation (non-synchronized shocks). The microprocessor 224 is capable of utilizing the therapeutic algorithms to determine what the most appropriate therapy is to employ. In an alternative embodiment, the decision may be made wholly by a user, or the microprocessor 224 may analyze the data and present a recommended therapeutic strategy to a user based on the analysis results. In this embodiment, the user ultimately decides which course of therapy to pursue.

Depending on what therapeutic decision is made, the method 300 proceeds to step 307, step 308, or step 309. For example, in the event a tachyarrhythmia in the ventricular-fibrillation range is detected at step 306, the method 300 proceeds directly to step 308, wherein the arrhythmia is treated by immediate defibrillation delivered by the MCD device 223. However, if tachycardia—particularly a slower one—is detected at step 306, the method 300 proceeds to step 307 and the arrhythmia is treated by sequences of overdrive pacing or low-energy cardioversion through the MCD system 200. However, if bradycardia is detected at step 306, the method 300 proceeds to step 309 and the MCD device 223 delivers antibradycardia pacing. While steps 307, 308, and 309 are illustrated as examples of therapeutic strategies, it will be recognized that the microprocessor 224 may be programmed by way of algorithms and other logic-based instructions to execute any desired therapeutic strategy using the MCD system 200.

After at least a small amount of magnetic energy has been applied to the myocardium at step 307, 308, or 309, the method 300 proceeds to step 310 wherein the echo and adjustment system 250 evaluates if the optimal therapeutic levels have been reached through feedback control. The use of the echo and adjustment system 250 in addition to the detection algorithm (e.g., Equations 1 and 2 where the geometrical positions of the MCD device 223 and coils 140 are known) initially utilizes a small amount of energy to stimulate the myocardial tissue and any resulting changes in the cardiac rhythm are evaluated. For example, depending on the feedback received through the leads 218 after the transmission of the first round of magnetic stimuli to the myocardium, the position and direction of the coils 140, the capacitor, and inductance may be adjusted to achieve optimal signal localization in the heart. Accordingly, at step 310, the echo and adjustment system 250 and the detection algorithm are used to assess the effects on the myocardial tissue of the magnetic stimuli delivered in step 307, 308, or 309. If the effects are not optimal, the placement of the MCD device 223 may be gradually adjusted until the optimal defibrillation level is achieved. In one embodiment, the robotic arm 400 may be used to automatically adjust the MCD device 223.

Once the MCD device 223 is optimally positioned and the appropriate parameters have been established, the therapy selected at step 306 is delivered by the MCD system 200 to correct the arrhythmia. At step 312, each of the electrograms collected by the leads 218 and analyzed by the microprocessor 224 are transferred to the memory device 226 for storage.

The foregoing embodiments have been presented for purposes of illustration and description and are not intended to be exhaustive or to limit the disclosed devices, systems, and methods to the precise forms disclosed. Many variations and modifications of the embodiments described herein will be apparent to one of ordinary skill in the art in view of this disclosure.

Further, in describing representative embodiments of the devices, systems and methods, the specification may have presented a method and/or process as a particular sequence of steps. However, to the extent that a method or process described herein does not rely on the particular order of steps set forth, the method or process should not be limited to the particular sequence of steps described. As one of ordinary skill in the art would appreciate, other sequences of steps may be possible. Therefore, the particular order of the steps set forth should not be construed as limitations on the claims. In addition, the claims directed to a method and/or process described herein should not be limited to the performance of its steps in the order written, and one skilled in the art can readily appreciate that the sequences may be varied and still remain within the spirit and scope of the disclosure.

The invention claimed is:

1. A device for stimulating a heart comprising:
a magnetic signal generator positioned relative to a heart, the magnetic signal generator comprising at least one coil to form a circuit;
a power supply coupled with the magnetic signal generator; and
a microprocessor in electrical communication with the power supply and operable to detect electrical activity information directly from the heart, process the information, and communicate with the magnetic signal generator;
wherein the magnetic signal generator is configured and operable to produce a magnetic signal that can stimulate an electrical activation in the heart, leadlessly transmit the magnetic signal to the heart, and function as a resynchronization device, defibrillator, or pacing device depending on instructions received from the microprocessor, the instructions based upon the information detected by the microprocessor directly from the heart.

2. The device of claim 1, wherein the at least one coil is configured into a circular flat-spiral coil.

3. The device of claim 1, wherein the at least one coil is configured into a butterfly shaped coil.

4. The device of claim 1, wherein the at least one coil is configured into a cloverleaf shaped coil.

5. The device of claim 1, wherein the device is positioned inside the chest cavity and the power supply is positioned subcutaneously.

6. The device of claim 1, wherein the microprocessor utilizes therapeutic algorithms to process the information to determine the instructions to communicate with the magnetic signal generator.

7. The device of claim 1, wherein the device is positioned outside the chest cavity.

8. A device for stimulating a heart, comprising:
a magnetic signal generator positioned relative to a heart, the magnetic signal generator comprising at least one coil to form a circuit, wherein the magnetic signal generator is configured and operable to produce a magnetic signal that can stimulate an electrical activation in the heart and leadlessly transmit the magnetic signal to the heart;
a power supply coupled to the magnetic signal generator;
a microprocessor in electrical communication with the power supply and operable to detect electrical activity information directly from the heart and communicate with the magnetic signal generator;
a memory device accessible by the microprocessor; and
a plurality of electrodes, each electrode having a first end and a second end, the first end electronically coupled with the microprocessor and the second end operable to detect the information;
wherein the microprocessor is capable of processing the information.

9. The device of claim 8, wherein the information is stored in the memory device.

10. The device of claim 8, wherein the magnetic signal generator can dictate the rhythm of the beating pattern of the heart.

11. The device of claim 8, wherein the device functions as a defibrillator.

12. The device of claim 11, wherein the device further functions as a resynchronization device.

13. The device of claim 11, wherein the device further functions as a pacing device.

14. The device of claim 8, wherein the device is located inside the chest cavity and the power supply is positioned subcutaneously.

15. A device for stimulating a heart, the device comprising:
  a magnetic signal generator positioned relative to a heart and comprising one or more coils;
  a power supply coupled with the magnetic signal generator; and
  a microprocessor in electrical communication with the power supply and operable to detect electrical activity information directly from the heart, process the information, and communicate with the magnetic signal generator;
  wherein the magnetic signal generator is configured and operable to produce a magnetic signal that can stimulate an electrical activation in the heart, transmit the magnetic signal to the heart, and function as a resynchronization device, defibrillator, or pacing device depending on instructions received from the microprocessor, the instructions based upon the information detected by the microprocessor directly from the heart.

16. The device of claim 15, wherein the magnetic signal is transmitted leadlessly.

17. The device of claim 15, wherein the magnetic signal generator is located inside the chest cavity and the power supply is positioned subcutaneously.

18. A system for stimulating a heart, the system comprising:
  a magnetic signal generator positioned relative to a heart, wherein the magnetic signal generator is configured and operable to produce a magnetic signal that can stimulate an electrical activation in the heart and leadlessly transmit the magnetic signal to the heart;
  a power supply coupled with the magnetic signal generator; and
  a microprocessor operable to detect electrical activity information directly from the heart, process the information, and communicate the frequency and strength of the magnetic signal the magnetic signal generator should transmit to the heart.

19. The system of claim 18, further comprising a device for receiving information from the heart.

20. The system of claim 19, wherein when the magnetic signal generator is positioned outside of a chest cavity, the device for receiving information is positioned within the chest cavity.

21. The system of claim 18, wherein the microprocessor is positioned adjacent to the heart.

22. The system of claim 18, wherein the microprocessor is positioned outside of a chest cavity.

23. The system of claim 18, further comprising a robotic arm for positioning the magnetic signal generator relative to the heart and in electrical communication with the microprocessor.

24. The system of claim 23, wherein the robotic arm comprises at least seven degrees of freedom.

25. The system of claim 18, wherein the system is capable of automatically monitoring the heart, determining what therapeutic treatment is optimal, and delivering the optimal therapeutic treatment to the heart.

26. The device of claim 8, wherein the microprocessor is capable of utilizing therapeutic algorithms to process the information detected from the heart and determining an optimal therapeutic treatment to employ.

27. The device of claim 26, wherein the communication between the microprocessor and the magnetic signal generator comprises treatment instructions based on the optimal therapeutic treatment determined by the microprocessor.

28. The device of claim 27, wherein the optimal therapeutic treatment comprises defibrillation.

29. The device of claim 27, wherein the optimal therapeutic treatment comprises resynchronization.

30. The device of claim 27, wherein the optimal therapeutic treatment comprises pacing.

31. The device of claim 28, wherein the optimal therapeutic treatment further comprises resynchronization.

32. The device of claim 31, wherein the optimal therapeutic treatment further comprises pacing.

33. The device of claim 27, wherein the microprocessor is capable of automatically sending updated treatment instructions to the magnetic signal generator based on information detected directly from the heart.

* * * * *